United States Patent [19]

Foggassy et al.

[11] Patent Number: 4,599,444
[45] Date of Patent: Jul. 8, 1986

[54] PROCESS FOR THE SEPARATION OF ISOMERIC CYCLOPROPANE-CARBOXYLIC ACIDS

[75] Inventors: Elemér Foggassy; Ferenc Faigl; Rudolf Soós; József Rákóczi, all of Budapest, Hungary

[73] Assignee: Chinoin Gyogyszer es Vegyeszeti Termekek Gyara Rt., Budapest, Hungary

[21] Appl. No.: 581,081

[22] Filed: Feb. 17, 1984

[30] Foreign Application Priority Data

Feb. 17, 1983 [HU] Hungary ................................ 551/83

[51] Int. Cl.$^4$ ............................................. C07B 57/00
[52] U.S. Cl. .............................. 562/401; 260/501.16; 260/501.17; 562/402; 562/506; 564/304
[58] Field of Search ...................... 562/401, 402, 506; 564/304; 260/501.16, 501.17

[56] References Cited

U.S. PATENT DOCUMENTS

| | | | |
|---|---|---|---|
| 3,842,125 | 10/1974 | Horiuchi et al. | 562/401 |
| 4,014,918 | 3/1977 | Martel | 562/401 X |
| 4,236,026 | 11/1980 | Naumann | 562/401 |
| 4,306,077 | 12/1981 | Leigh | 562/401 |
| 4,327,038 | 4/1982 | Suzuki | 562/401 |

*Primary Examiner*—Natalie Trousof
*Assistant Examiner*—Vera C. Clarke
*Attorney, Agent, or Firm*—Karl F. Ross; Herbert Dubno

[57] ABSTRACT

The invention relates to a new process for separating the four stereoisomers of the cyclopropanecarboxylic acids of the formula

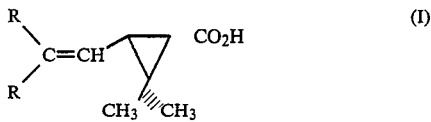

wherein
R stands for a methyl group or a halogen atom.

The process comprises
reacting a salt formed with an alkali hydroxide or an alkali carbonate of dl-cis-trans-2,2-dimethyl-3-(2,2-disubstituted vinyl)-cyclopropanecarboxylic acids containing the isomers in any ratio or the pure dl-cis and dl-trans-2,2-dimethyl-3-(2,2-disubstituted vinyl)-cyclopropanecarboxylic acids prepared therefrom by the means of a selective dissolution with aromatic and aliphatic hydrocarbon solvents (suitably with benzene, extraction petroleum ether, n-hexane) with N-benzyl-2-aminobutanol enantiomers or with the hydrochlorides thereof in an aqueous medium or aqueous acetone medium, obtaining the crystalline diastereomeric salt from the solution by filtration, decomposing said salt by using a mineral acid, then separating the thus obtained optically active cyclopropanecarboxylic acid and obtaining the other isomer or other mixture of isomers from the filtrate of the said diastereomeric salt similarly after acidifying by a mineral acid, if desired, purifying the said optically active 2,2-di-methyl-3-(2,2-disubstituted vinyl)-cyclopropane-carboxylic acid isomers obtained by the above-mentioned procedure by a selective precipitation and recovering the resolving agent.

19 Claims, No Drawings

PROCESS FOR THE SEPARATION OF ISOMERIC CYCLOPROPANE-CARBOXYLIC ACIDS

This invention relates to a new process for separating the four stereoisomers of the cyclopropanecarboxylic acids of the formula

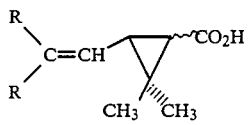

wherein
R stands for a methyl group or a halogen atom.

Surprisingly, it has been found in the course of our work that the enantiomeric d-N-benzyl-2-aminobutanol and l-N-benzyl-2-aminobutanol are particularly useful for separating the d-trans, l-trans and dl-cis isomers from the racemic cis-trans-cyclopropanecarboxylic acids of the formula (I). Further on, it has been found that the solubility in some solvents of the racemic cis- and racemic trans-cyclopropanecarboxylic acids is significantly different thus, under given conditions those can be separated from another in a practically quantitative yield, in an easily realizable way on an industrial scale. The enantiomers of the cis and trans racemates obtained can be separated with a high selectivity by means of the enantiomeric N-benzyl-2-aminobutanols.

The compounds of the formula (I) are intermediates for the production of the pyrethroid insecticides. The biological activity of the pyrethroids remarkably depends on the stereochemistry of the carboxylic acid of the formula (I) used for the synthesis thus, a highly efficient separation of the optical isomers has a great technical (industrial) importance.

The separation of the racemic cis- and racemic trans-2,2-dimethyl-3-(2,2-dichlorovinyl)-cyclopropanecarboxylic acid (further on: permethric acid) isomers by several recrystallizations from n-hexane has been published (Coll. Czech. Chem. Commun. 24, 2230). A yield of 30% was obtained by enriching dl-trans-permethric acid in the crystalline phase. The cis and trans isomers of cyclopropanecarboxylic acids were separated by fractional distillation as described in the DE-PS (West German Patent Specification) No. 2 716 898. The geometrical isomers of substituted cyclopropanecarboxylic acids were separated by extracting their aqueous solutions with an apolar organic solvent according to the DE-PS (West German Patent Specification) No. 2 713 538.

Several processes have also been published for the separation of the racemic cis- and racemic trans-2,2-dimethyl-3-(2-methyl-propen-1-yl)-cyclopropanecarboxylic acid (further on: chrysanthemic acid) isomers. These isomers were separated e.g. by recrystallization from petroleum ether (Helv. Chim. Acta 7, 396) or from ethyl acetate [J. Am. Chem. Soc. 67, 238 (1945)].

A drawback of the methods mentioned above consists in that the pure cis and trans isomers can only be obtained by several recrystallizations and thus, with high losses of material.

A number of methods for the separation of the optical isomers of cyclopropanecarboxylic acids of the formula (I) are also known. According to the DE-PS (West German Patent Specification) No. 2 826 952 trans-permethric acid is resolved by using (-)-phenylglycine ethyl ester. Optically active naphthylethylamine, cinchonidine, quinine and N,N-dimethyl-1-(4-nitrophenyl)-2-amino-1,3-propanediol enantiomers are employed as resolving agents in the course of other processes (Hungarian Pat. No. 158 498 as well as British Pat. Nos. 1 369 730, 1 226 914 and 1 178 423).

The disadvantages of these processes consist in the use of expensive resolving agents and costly accomplishments suitable only for the separation of either one of the racemates or of the cis or trans pair of enantiomers. For increasing the optical purity of the enantiomers recrystallization is used which is an expensive process causing high material losses; the recovery (regeneration) of the resolving agent is not published.

In general, the processes employed for the industrial synthesis of the cyclopropanecarboxylic acids of the formula (I) lead to the mixtures of dl-cis-trans isomers.

Thus, the separation of the four isomers—in order to obtain pyrethroids with a more favorable insecticidal action involves an important industrial and economical task.

The object of the present invention is to solve this problem.

Our invention is based on the recognition that the enantiomeric N-benzyl-2-aminobutanols are particularly useful for the separation of the enantiomers from an isomeric mixture containing the cyclopropanecarboxylic acids of the formula (I) in any ratio.

Thus, e.g. out of the racemic cis-trans-permethric acid, d-trans-permethric acid gives a crystalline diastereomeric salt with d-N-benzyl-2-aminobutanol in an aqueous medium, in the presence of an appropriate amount of an alkali hydroxide or alkali carbonate when the resolving agent is added in a quantity equivalent to this enantiomer. The l-trans isomer can also be obtained from the l-trans-dl-cis-permethric acid remaining in the filtrate of the resolution by adding to the solution l-N-benzyl-2-aminobutanol equivalent to the l-trans isomer. Finally, it has been stated that the optical isomers of the residual dl-cis-permethric acid can also be separated with a high efficiency by using the enantiomeric N-benzyl-2-aminobutanols. It is surprising, however, that in this case l-cis-permethric acid forms a crystalline diastereomeric salt with d-N-benzyl-2-aminobutanol when the resolution is carried out in an alkaline medium, preferably at a pH value of 8 to 8.5.

A main part of our process also consists in the observation that the resolving agent used by us is remarkably useful for the separation of the optical isomers of both the pure dl-cis- and dl-trans-permethric acids as well as of the dl-cis- and dl-trans-chrysanthemic acids. An advantage of our method is therefore that the resolution of each racemate is accomplished in aqueous solutions under nearly identical conditions thus, our method is more simple, versatile and efficient than the processes known so far.

If desired, the dl-cis- and dl-trans-permethric acids and dl-cis- and dl-trans-chrysanthemic acids, respectively can be prepared from the cis-trans mixtures for the resolutions on the basis of our observation that the solubility in certain solvents of the isomers is highly different.

Surprisingly, it has been found that the amounts related to each other of the starting cis-trans isomers can be modified in the desired direction and to the desired extent, practically independently of the starting ratio.

When the aim is to increase the relative amount of dl-cis-permethric acid, this can be reacted by stirring thoroughly with an appropriate amount of benzene at 20° to 30° C. Surprisingly, it has been found that, when the stirring is continued at the given temperature for a suitable period, then the proportion in the filtered material of dl-cis-permethric acid less soluble in benzene is only dependent upon the amount of the solvent used after reaching the solubility equilibrium. By augmenting the ratio of benzene to the permethric acid, the amount of cis isomer significantly increases in the solid phase. The ratio of isomers of the substances enriched of the trans isomer obtained by evaporating the solution is practically identical, therefore these materials of the second crop obtained during enrichments of the cis isomer can be combined and used, when desired, for the preparation of the pure dl-trans isomer.

The pure dl-trans-permethric acid is obtained by stirring thoroughly the materials which are rich in the trans isomer and prepared as described above, with an appropriate amount of apolar solvents, preferably extraction petroleum ether or n-hexane. It has been surprisingly found in this case that the relative amount of dl-trans-permethric acid in the filtered material changes in a direct ratio with the volume of the aliphatic hydrocarbon solvent used for a weight unit of the mixture of isomers. Simultaneously, the isomer ratio of the substances isolated from the filtrates is in nearly all cases identical thus, these can be combined and used for the further separation. Therefore, according to our observations a mixture of cis-trans-permethric acid with an optional composition can be separated with a nearly quantitative yield to the dl-cis and dl-trans isomeric components by using alternatively an aromatic solvent, preferably benzene and an aliphatic hydrocarbon, preferably extraction petroleum ether or n-hexane.

Peculiarly, when R in the formula (I) stands for a methyl group, i.e. the aim is to separate the cis and trans isomers of dl-cis-trans-chrysanthemic acid, then the isolation of the dl-cis isomer can be solved in a relatively more simple way because of the higher difference in the solubilities of these isomers. Our observation that these substances do not influence the solubility of each other, is also peculiar. Thus, if desired, the use of the aromatic solvent can be omitted on separating the cis- and trans isomers of chrysanthemic acid. The cis isomer is obtained from the solid material remaining after the stirring with an aliphatic hydrocarbon solvent, preferably with n-hexane. The trans isomer is prepared in a somewhat more difficult way than are obtained the derivatives described above, i.e. by the repeated treatment with an aliphatic hydrocarbon solvent of the material obtained by evaporating the filtrate. The separation can be carried out with a nearly quantitative yield by the repeated use of the solutions in this case, too.

However, it has surprisingly been found that the solubilities of the isomeric acids and those of their sodium salts are opposite thus, dl-trans-chrysanthemic acid can primarily obtained as a pure isomer from the mixture of isomers by forming the sodium salt in aqueous acetone, filtrating out the dl-trans salt and transforming it to the acid in the usual way.

Thus, according to our invention, the resolution of dl-cis- and dl-trans-permethric acids and of chrysanthemic acids, respectively are also accomplished by using the N-benzyl-2-aminobutanol enantiomers with the addition of 0.4 to 0.6 equivalent of the resolving agent to an aqueous solution of the appropriate racemic acid prepared with 1.0 to 1.3 equivalent of an alkali hydroxide or of an alkali carbonate, suitably at a temperature of 40° to 90° C. A solution of the resolving agent in acetone or of its hydrochloride in aqueous acetone is used. Then, the reaction mixture is allowed to cool and the crystalline diastereomeric salt is separated by filtration.

When d-N-benzyl-2-aminobutanol is used as resolving agent, the diasteromeric salt of the following acids crystallizes out from the solution: the d-trans isomer by resolving dl-trans-permethric acid; the l-cis enantiomer by resolving dl-cis-permethric acid; d-trans-chrysanthemic acid by resolving dl-trans-chrysanthemic acid; and l-cis-chrysanthemic acid by resolving dl-cis-chrysanthemic acid.

When l-N-benzyl-2-aminobutanol is used as resolving agent, the appropriate opposite antipode crystallizes in all cases.

The diastereomeric salts described here are new compounds which are so far unknown in the literature.

According to our observations, the optical purity of the enantiomer contained in the diastereomeric salt is strongly dependent upon the hydrogen ion concentration of the medium for resolution thus, from the viewpoint of the efficiency it is essential to comply accurately with the quantity of the base used for dissolving the racemic acids and similarly, with that of the acid used for dissolving the resolving agent, if necessary. According to our experiments, the optimum separation in the resolution of all cyclopropanecarboxylic acids of the formula (I) can be accomplished by using 1.0 to 1.3, preferably 1.2 equivalents of the base as calculated for the racemic acid.

Our discovery that, if necessary, the optical purity of the optically active cis- and trans-permethric and chrysanthemic acid isomers obtained by using the resolving agent can be increased by a selective precipitation, is also a subject of our invention. Namely, when a mineral acid, calculated on the basis of the optical purity of the acid but in an amount less than an equivalent is added at a temperature of 0° to +10° C. to the solution of any of these optically active carboxylic acids prepared with an alkali hydroxide, then the optical purity of the separated crystalline acid fraction will be highly different from that of the part remaining in the solution as well as from the starting optical purity. It can be reached by using this method that the one fraction will contain a nearly racemic compound, while the other one the optically active carboxylic acid. The racemic proportion can again be used for resolution.

The economy of our process is also increased by the fact that the resolving agent used can be recovered simply and with nearly quantitative yield from the aqueous acidic solutions deriving from the resolutions.

The present invention is illustrated in the following Examples, however, without limiting the process of our invention thereto.

EXAMPLE 1

(a) 10.5 g. of a racemic mixture of cis-trans-permethric acid isomers (consisting of 40% cis and 60% trans isomer) were dissolved in a solution of 2.4 g. of sodium hydroxide in 60 ml. of water, heated to 60° C. and at the same temperature a solution containing 2.3 g. of d-N-benzyl-2-aminobutanol in 10 ml. of acetone were added. The mixture was allowed to cool while stirring and inoculated with 0.1 g. of the d-trans-permethric acid d-N-benzyl-2-aminobutanol salt. After setting aside for 3 hours at 25° C. the product was filtered and washed with 2×5 ml. of water to give 3.5 g. of the salt.

This salt was suspended in the mixture of 10 ml. of water with 20 ml. of chloroform, the mixture was cooled to 10° C. and acidified to pH 1 by 5N hydrochloric acid. After 15 minutes the two phases were separated, the aqueous solution was extracted with 10 ml. of chloroform, the combined chloroformic solutions were dried over anhydrous sodium sulphate and filtered. The filtrate was evaporated under reduced pressure. The residue was 1.85 g. (63%) of d-trans-permethric acid, m.p. 53°–61° C. $[\alpha]_D^{25}+34°$ (c=1.8, chloroform). The filtrate of the resolution was evaporated to one-third volume under reduced pressure, the residue diluted with 10 ml. of water and acidified to pH 1 by 5N hydrochloric acid. The separated oil was extracted with 2×20 ml. of chloroform, the combined organic phase was dried over anhydrous sodium sulphate, filtered and the filtrate evaporated to give as a residue 8 g. of l-trans-dl-cis-permethric acid, m.p. 53°–65° C. $[\alpha]_D^{25}-6.7°$ (c=2, chloroform.)

(b) The procedure described in Example (1a) was followed except that the racemic permethric acid was dissolved by using 4.2 g. of sodium hydrogen carbonate instead of sodium hydroxide. In this case 1.65 g. of d-trans-permethric acid were obtained from the salt, $[\alpha]_D^{25}+33°$ (c=2, chloroform). The filtrate of the resolution gave 7 g. of l-trans-dl-cis-permethric acid, $[\alpha]_D^{25}-7°$ (c=2, chloroform).

(c) The procedure described in Example (1a) was followed except that the racemic permethric acid was dissolved by using 5.3 g. of sodium carbonate instead of sodium hydroxide. The salt gave 2.0 g. of d-trans-permethric acid, $[\alpha]_D^{25}+38°$ (c=2, chloroform). From the filtrate of the resolution 7.5 g. of l-trans-dl-cis-permethric acid were obtained, $[\alpha]_D^{25}-7.8°$ (c=1.6, chloroform).

EXAMPLE 2

(a) 100 g. of dl-cis-trans-permethric acid (consisting of 40% cis and 60% trans isomer) were stirred with 400 ml. of benzene at 27° for one hour, then the suspension was filtered. The solid product, i.e. 31 g. of permethric acid consisting of 79% cis and 21% trans isomer was worked up according to the Example (4b) for obtaining racemic cis-permethric acid. The benzene solution was evaporated to give 67.2 g. of a mixture consisting of 23% cis and 77% trans isomer which was then stirred together with extraction petroleum ether at 30° C. for 5 hours. The suspension was filtered to give 26.8 g. of dl-trans-permethric acid as a solid product containing more than 95% trans isomer.

The filtrate containing extraction petroleum ether was evaporated to give 40 g. of permethric acid consisting of 38% cis-and 62% trans isomer which was used as a starting material for the separation of the dl-cis and dl-trans isomers.

(b) 10.5 g. of dl-trans-permethric acid prepared as described in Example (2a) were dissolved in a solution of 2.2 g. of sodium hydroxide in 60 ml. of water. After heating this solution to 70° C., a mixture containing 4.5 g. of d-N-benzyl-2-aminobutanol, 20 ml. of acetone, 10 ml. of water and 2.5 ml. of 10N hydrochloric acid was added. The mixture obtained was cooled to 25° C. with stirring, then set aside at this temperature for 10 hours. The precipitated crystals were filtered, washed with 2×5 ml. of water and dried to give 6.0 g. of the diastereomeric salt.

This salt was suspended in the mixture of 10 ml. of water and 20 ml. of chloroform and acidified to pH 1 by 5N hydrochloric acid. The organic phase was separated and the aqueous solution was extracted with 10 ml. of chloroform. The chloroformic solutions were combined, dried over anhydrous sodium sulphate and evaporated to dry to give as a residue 3.1 g. of d-trans-permethric acid, $[\alpha]_D^{25}+35°$ (c=2.5, chloroform).

The filtrate of the resolution was evaporated under reduced pressure and the residue worked up similarly to the salt to give 7.2 g. of l-trans-permethric acid, $[\alpha]_D^{25}-17.5°$ (c=2, chloroform).

(c) A solution of 10.5 g. of dl-trans-permethric acid in 50 ml. of water containing 2.4 g. of sodium hydroxide was heated to 80° C. and a mixture containing 4.5 g. d-N-benzyl-2-aminobutanol, 2.5 ml. of 10N hydrochloric acid and 20 ml. of water was added. Further on, the procedure described in Example (2b) was followed to give 4.0 g. of d-trans-permethric acid. As the resolving mixture contained no acetone, l-trans-permethric acid was obtained without any preliminary evaporation, by acidifying the filtrate of the resolution to pH 1. Thus, 6.0 g. of product were obtained, $[\alpha]_D^{25}-13°$ (c=1.9, chloroform).

EXAMPLE 3

(a) 100 g. of dl-cis-trans-chrysanthemic acid (consisting of 40% cis and 60% trans isomer) were stirred together with 45 ml. of n-hexane at 25° C. for one hour. The suspension was filtered to give 35.3 g. of chrysanthemic acid as a solid product containing 80% cis and 20% trans isomer. After evaporation of the filtrate, 62 g. of chrysanthemic acid containing 18% cis and 82% trans isomer were obtained which was stirred together with 35 ml. of n-hexane at 25° C. for 30 minutes and the undissolved mixture enriched of the cis isomer was filtered from the solution. The filtrate was evaporated to half its volume and stirred again at 0° C. for one hour. The separated crystals were filtered and the stirring described above was repeated to give 9.1 g. of dl-trans-chrysanthemic acid containing 99.8% trans isomer, m.p. 52°–54° C.

(b) A solution of 3.36 g. of dl-trans-chrysanthemic acid in 15 ml. of water containing 0.95 g. of sodium hydroxide was heated to 60° C. and to this solution a mixture containing 1.8 g. of d-N-benzyl-2-aminobutanol, 5 ml. of 2N hydrochloric acid and 10 ml. of water and then 10 ml. of acetone were added. The mixture was allowed to cool to 25° C., after 2 hours the crystals were filtered out and washed with 2×2 ml. of water to give 3.5 g. of the diastereomeric salt. The suspension of this salt in the mixture of 10 ml. of water and 20 ml. of chloroform was acidified by 5N hydrochloric acid to pH 1. The organic layer was separated from the aqueous phase, dried over anhydrous sodium sulphate and chloroform was evaporated under reduced pressure to give as a residue 1.6 g. of d-trans-chrysanthemic acid, $[\alpha]_D^{25} +20°$ (c=1.8, chloroform).

The filtrate of the resolution was evaporated to the half volume, the residue was diluted with 10 ml. of water and acidified by 5N hydrochloric acid to pH 1. The separated oil was extracted into 20 ml. of chloroform, the organic solution dried over anhydrous sodium sulphate and evaporated to give as a residue 1.6 g. of l-trans-chrysanthemic acid, $[\alpha]_D^{25} -20°$ (c=2, chloroform).

EXAMPLE 4

(a) 100 g. of dl-cis-trans-permethric acid (consisting of 40% cis and 60% trans isomer) were stirred together with 500 ml. of benzene at 30° C. for 5 hours. Filtration of the suspension resulted in 23 g. of a solid product containing 97.5% cis isomer. If necessary, this substance was recrystallized from 70 ml. of benzene to give 18.4 g. of dl-cis-permethric acid containing 99.8% cis isomer, m.p. 86.9°–88° C. The filtrate derived from the stirring with benzene was evaporated to give 75 g. of permethric acid consisting of 24% cis and 76% trans isomer which could be used for the preparation of the dl-trans isomer according to the procedure described in Example 2.

(b) 31.0 g. of an isomeric mixture of permethric acid obtained by using the procedure described in Example (2a) and consisting of 79% cis and 21% trans isomer were stirred together with 120 ml. of benzene at 27° C. for 5 hours. The suspension was filtrated to give 27.7 g. of a solid product containing 98.1% cis isomer. If necessary, this substance was recrystallized from 70 ml. of benzene to give 18.1 g. of dl-cis-permethric acid with a purity of 99.8%.

The filtrate derived from the stirring with benzene was evaporated to give 2.6 g. of permethric acid consisting of 24% cis and 76% trans isomer which could be used for the preparation of the dl-trans isomer according to the procedure described in Example 2.

(c) 10.5 g. of dl-cis-permethric acid prepared as described in Example (4a) and (4b), respectively were added to the solution of 2.2 g. of sodium hydroxide in 50 ml. of water and heated to 60° C. To this solution containing the sodium salt of the permethric acid, a mixture containing 4.5 g. of d-N-benzyl-2-aminobutanol, 10 ml. of water, 10 ml. of acetone and 2.5 ml. of 10N hydrochloric acid was added. While cooling, crystals began to separate from the solution. After 10 hours the crystalline salt was filtered and washed with 2×5 ml. of water. The obtained salt (4.0 g.) was suspended in the mixture of 10 ml of water and 20 ml. of chloroform, acidified to pH 1, the organic layer was separated from the aqueous solution, dried over anhydrous sodium sulphate and evaporated to give 2.3 g. of l-cis-permethric acid, m.p. 82°–85° C., $[\alpha]_D^{25} -24°$ (c=2.1, chloroform).

(When the acidification is made below +10° C., the extraction can be omitted as the product precipitated in a crystalline form.)

The filtrate of the resolution was evaporated to one-third its volume, the residue was diluted with 10 ml. of water and acidified to pH 1 at +10° C. by 5N hydrochloric acid. After one hour the precipitated crystalline product was filtered and washed with 3×5 ml. of water to yield 8.0 g. of d-cis-permethric acid, m.p. 78°–82° C., $[\alpha]_D^{25} +4.2°$ (c=1.6, chloroform).

EXAMPLE 5

(a) 35.3 g. of chrysanthemic acid obtained by using the procedure described in Example (3a) and containing 80% cis isomer were stirred together with 50 ml. of n-hexane at 25° C. for 30 minutes and filtered. The crystals remaining on the filter were washed with 10 ml. of n-hexane cooled to 0°–5° C. The wet product was recrystallized from 75 ml. of methanol to give 20.4 g. of dl-cis-chrysanthemic acid containing 99.8% cis isomer, m.p. 114°–116° C.

From the hexane solutions the cyclopropanecarboxylic acid rich in the trans isomer was recovered by evaporation and used again for the separation of the isomers.

(b) 3.36 g. of dl-cis-chrysanthemic acid prepared as described in Example (5a) were dissolved in 15 ml. of water containing 0.9 g. of sodium hydroxide, heated to 65° C. and a mixture containing 1.79 g. of d-N-benzyl-2-aminobutanol, 5 ml. of water and 5 ml. of 2N hydrochloric acid was added. The mixture was allowed to cool to 25° C. and the precipitated crystalline diasteromeric salt was filtered after 2 hours. The salt weighing 3.3 g. was suspended in a mixture of 10 ml. of water and 20 ml. of chloroform and the suspension was acidified to pH 1 by 5N hydrochloric acid. The organic phase was separated, dried over anhydrous sodium sulphate and evaporated to give as a residue 1.6 g. of l-cis-chrysanthemic acid, $[\alpha]_D^{25} -50°$ (c=2, chloroform).

The filtrate of the resolution was worked up similarly to the salt and resulted in 1.4 g. of d-cis-chrysanthemic acid, $[\alpha]_D^{25} +47°$ (c=2.1, chloroform).

EXAMPLE 6

8.0 g. of l-trans-dl-cis-permethric acid prepared as described in Example (1a) were dissolved in 60 ml. of water containing 1.6 g. of sodium hydroxide, heated to 70° C. and a mixture containing 2.6 g. of l-N-benzyl-2-aminobutanol hydrochloride dissolved in 7 ml. of water were added. The mixture was let cool to 25° C. and stay for additional 2 hours. The precipitated l-trans-permethric acid l-N-benzyl-2-aminobutanol salt was filtered and washed with 2×5 ml. of water to give a yield of 4.0 g.

The working up of this salt according to the Example (1a) resulted in 2.0 g. of l-trans-permethric acid, $[\alpha]_D^{25} -30°$ (c=2, chloroform).

The filtrate of the resolution was acidified to pH 1 by 5N hydrochloric acid. After extracting the separated oil into 20 ml. of chloroform, the organic phase was dried over anhydrous sodium sulphate and evaporated to give as a residue 5.2 g. of dl-permethric acid which was rich in the cis isomer. The enantiomers were obtained from this acid according to the Example 4.

EXAMPLE 7

(a) 6.0 g. of l-trans-permethric acid/$[\alpha]_D^{25} -17.5°$ (c=2, chloroform)/were dissolved in a mixture containing 12 ml. of sodium hydroxide of 10% and 5 ml. of water, cooled to +10° C. and 5 ml. of 2N hydrochloric acid were added. The precipitated crystalline substance was filter to give 2.3 g. of product, $[\alpha]_D^{25} -25°$ (c=2, chloroform). The filtrate was acidified to pH 1 and the precipitated substance was filtered to give 3.4 g. of acid, $[\alpha]_D^{25} -8.0°$ (c=2.1, chloroform).

(b) 2.0 g. of l-trans-permethric acid ($[\alpha]_D^{25} -25°$ (c=2, chloroform)) were dissolved in a mixture containing 4 ml. of sodium hydroxide of 10% and 1.6 ml. of water, cooled to +10° C. and 1.6 ml. of 2N hydrochloric acid were added. The precipitated crystalline substance was filtered to give 0.75 g. of product, $[\alpha]_D^{25} -38°$ (c=2, chloroform). The filtrate was acidified to pH 1, filtered and dried to give 1.15 g. of nearly racemic trans-permethric acid, $[\alpha]_D^{25} -8.5°$ (c=1.9, chloroform), which could again be used for resolution.

EXAMPLE 8

8.8 g. of d-cis-permethric acid ($[\alpha]_D^{25} +24°$ (c=2, chloroform)) were dissolved in a mixture containing 17 ml. of sodium hydroxide of 10% and 10 ml. of water, cooled to +10° C. and 5 ml. of 2N hydrochloric acid were added. After filtering the precipitated product 2.4 g. were obtained, $[\alpha]_D^{25} +5.5°$ (c=2, chloroform). The filtrate was acidified to pH 1 by hydrochloric acid, the precipitated crystals were filtered, washed with 2×5 ml. of water and dried to give 6.0 g. of product, $[\alpha]_D^{25} +26°$ (c=2.1, chloroform).

EXAMPLE 9

62 g. of chrysanthemic acid (consisting of 18% cis and 82% trans isomer) prepared as described in Example (3a) and enriched in the trans isomer were dissolved at 70°–75° C. in 70 ml. of a 20% aqueous sodium hydroxide solution, cooled to room temperature and set aside overnight. The precipitated crystals were filtered by thorough suction and dissolved in 330 ml. of water, 240 ml. of petroleum ether (b.p. 40° C.) were added to the solution of the sodium salt obtained and the mixture was acidified to pH 1 by concentrated hydrochloric acid while stirring. The organic phase was separated and the aqueous solution was again extracted with 75 ml. of petroleum ether. After combination, the organic solution was washed with 3×100 ml. of water, dried over anhydrous sodium sulphate, then evaporated to one-fourth its volume. The obtained solution was slowly cooled to 25° C. and stirred at this temperature for one hour. After filtering out a little amount of the crystals rich in the cis isomer, the mother liquor was further cooled to −10° C. and the precipitated crystals were separated. Thus 23.1 g. of dl-trans-chrysanthemic acid were obtained with a purity of 99.8% which was resolved according to the Example (3b).

EXAMPLE 10

The resolving agent present in the acidic aqueous solutions obtained from the salts of the resolutions as well as from the working up of the mother liquors, was recovered as follows.

The traces of the organic solvents were removed by clarifying with activated carbon by boiling for 10 minutes, then the solution was cooled to +15° C. and made alkaline to pH 11 by 5N sodium hydroxide solution. After cooling by ice for one hour, the crystalline suspension was filtered, the precipitate was washed three times with water and dried. In this way 85 percent of the N-benzyl-2-aminobutanol enantiomers were recovered.

We claim:

1. A process for preparing the optically active cis and trans isomers of the cyclopropanecarboxylic acids of the formula

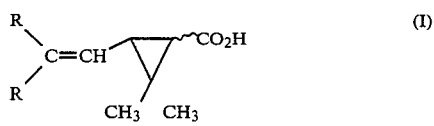

wherein
R stands for a methyl group or a halogen atom, which comprises,
reacting a salt formed with an alkali hydroxide or an alkali carbonate of dl-cis-trans-2,2-dimethyl-3-(2,2-disubstituted vinyl)-cyclopropanecarboxylic acids containing the isomers in any ratio or the pure dl-cis and dl-trans-2,2-dimethyl-3-(2,2-disubstituted vinyl)-cyclopropanecarboxylic acids prepared therefrom by the means of a selective dissolution with aromatic and aliphatic hydrocarbon solvents with N-benzyl-2-aminobutanol enantiomers or with the hydrochlorides thereof in an aqueous medium or aqueous acetone medium obtaining the crystalline diastereomeric salt from the solution by filtration, decomposing said salt by using a mineral acid, then separating the thus obtained optically active cyclopropanecarboxylic acid.

2. A process as claimed in claim 1 for preparing d-trans-2,2-dimethyl-3-(2,2-disubstituted vinyl)-cyclopropanecarboxylic acid, which comprises—reacting an aqueous solution of the salt of the racemic acid, containing the cis-trans isomers in any ratio, formed with 1.0 to 1.3 equivalents of an alkali hydroxide with d-N-benzyl-2-aminobutanol taken in an amount equivalent to the d-trans isomer content of said racemate and dissolved in an aliphatic ketone at a temperature of 40° to 60° C., obtaining the crystalline d-trans-2,2-dimethyl-3-(2,2-disubstituted vinyl)-cyclopropanecarboxylic acid d-N-benzyl-2-aminobutanol salt after cooling by filtration and proceeding further on according to claim 1.

3. A process as claimed in claim 1 for preparing d-trans-2,2-dimethyl-3-(2,2-disubstituted vinyl)-cyclopropanecarboxylic acids, which comprises—obtaining the dl-trans-carboxylic acid in a high purity from the appropriate dl-cis-trans-2,2-dimethyl-3-(2,2-disubstituted vinyl)-cyclopropane-carboxylic acid by stirring together with an aromatic hydrocarbon, and with an aliphatic hydrocarbon, at 25° to 30° C., by using the solvents alternatively, then reacting the aqueous solution of said acid prepared with 1.0 to 1.3 equivalents of an alkali hydroxide at a temperature of 40° to 90° C. with an aqueous solution of 0.4 to 0.6 equivalent of d-N-benzyl-2-aminobutanol hydrochloride containing also acetone, then obtaining the crystalline d-trans-2,2-dimethyl-3-(2,2-disubstituted vinyl)-cyclopropanecarboxylic acid salt after cooling by filtration, and proceeding further on according to claim 1.

4. A process as claimed in claim 1 for preparing l-cis-2,2-dimethyl-3-(2,2-disubstituted vinyl)-cyclopropanecarboxylic acids, which comprises—obtaining the racemic cis isomer in a high purity from the residue remaining after stirring the dl-cis-trans-2,2-dimethyl-3-(2,2-disubstituted vinyl)-cyclopropanecarboxylic acid with an aromatic hydrocarbon, and with an aliphatic hydrocarbon, by using the solvents alternatively, then adding an aqueous acetone solution of 0.4 to 0.6 equivalent of d-N-benzyl-2-aminobutanol hydrochloride at a temperature of 40° to 90° C. to an aqueous solution of the obtained racemic cis isomer prepared with 1.0 to 1.3 equivalents of an alkali hydroxide or alkali carbonate, then separating the crystalline l-cis-2,2-dimethyl-3-(2,2-disubstituted vinyl)-cyclopropanecarboxylic acid salt after cooling by filtration, and proceeding further on according to claim 1.

5. A process for the preparation of a d-trans-2,2-dimethyl-3-(2,2-vinyl)-cyclopropane carboxylic acid of the formula (I)

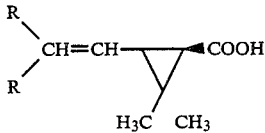

wherein
R is methyl or halogen;
which comprises the steps of:
(a) reacting in an aqueous solution an isomeric mixture of a 2,2-dimethyl-3-(2,2-vinyl)-cyclopropane carboxylic acid containing dl-trans-2,2-dimethyl-3(2,2-vinyl)-cyclopropane carboxylic acid with 1.2 to 1.3 equivalents of an alkali hydroxide or alkali carbonate to form a salt thereof;

(b) treating the alkali salt formed during the step (a) with an equimolar amount of d-N-benzyl-2-aminobutanol to the amount of the d-trans isomer present in the isomeric mixture to form the d-trans-2,2-dimethyl-3(2,2-vinyl)-cyclopropane carboxylic acid-d-N-benzyl-2-amino-butanol as a crystalline salt;

(c) filtering the crystalline salt from the solution containing the optically active antipode;

(d) applying a mineral acid to decompose the crystalline salt; and (e) recovering the d-trans-2,2-dimethyl-3-(2,2-vinyl)-cyclopropane carboxylic acid.

6. A process for the preparation of a l-cis-2,2-dimethyl-3-(2,2-vinyl)-cyclopropane carboxylic acid of the formula (I)

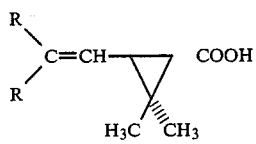

wherein
R is methyl or halogen; which comprises the steps of:
(a) reacting in an aqueous solution an isomeric mixture of a 2,2-dimethyl-3-(2,2-vinyl)-cyclopropane carboxylic acid containing a dl-cis-2,2-dimethyl-3-(2,2-vinyl)-cyclopropane carboxylic acid with 1.2 to 1.3 equivalents of an alkali hydroxide or alkali carbonate to form a salt thereof;

(b) treating the alkali salt formed during step (a) with an equimilar amount of d-N-benzyl-2-aminobutanol to the amount of the l-cis isomer present in the isomeric mixture to form the l-cis-2,2-dimethyl-3-(2,2-vinyl)-cyclopropane carboxylic acid-d-N-benzyl-2-amino-butanol as a crystalline salt;

(c) filtering the crystalline salt from the solution containing the optically active antipode;

(d) applying a mineral acid to decompose the crystalline salt; and (e) recovering the l-cis-2,2-dimethyl-3-(2,2-vinyl)-cyclopropane carboxylic acid.

7. A process for the preparation of a d-cis-2,2-dimethyl-3-(2,2-vinyl)-cyclopropane carboxylic acid of the formula (I)

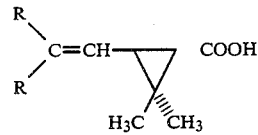

wherein
R is methyl or halogen;
which comprises the steps of:
(a) reacting in an aqueous solution an isomeric mixture of a 2,2-dimethyl-3-(2,2-vinyl)-cyclopropane carboxylic acid containing a dl-cis-2,2-dimethyl-3-(2,2-vinyl)-cyclopropane carboxylic acid with 1.2 to 1.3 equivalents of an alkali hydroxide or alkali carbonate to form a salt thereof;

(b) treating the alkali salt formed during step (a) with an equimolar amount of l-N-benzyl-2-aminobutanol to the amount of the d-cis isomer present in the isomeric mixture to form the d-cis-2,2-dimethyl-3(2,2-vinyl)-cyclopropane carboxylic acid-l-N-benzyl-2-amino-butanol as a crystalline salt;

(c) filtering the crystalline salt from the solution containing the optically active antipode;

(d) applying a mineral acid to decompose the crystalline salt; and (e) recovering the d-cis-2,2-dimethyl-3-(2,2-vinyl)-cyclopropane carboxylic acid.

8. A process for the preparation of a l-trans-2,2-dimethyl-3-(2,2-vinyl)-cyclopropane carboxylic acid of the formula (I)

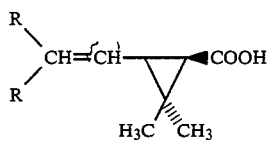

wherein
R is methyl or halogen;
which comprises the steps of:

(a) reacting in an aqueous solution an isomeric mixture of a 2,2-dimethyl-3-(2,2-vinyl)-cyclopropane carboxylic acid containing a dl-trans-2,2-dimethyl-3-(2,2-vinyl)-cyclopropane carboxylic acid with 1.2 to 1.3 equivalents of an alkali hydroxide or alkali carbonate to form a salt thereof;

(b) treating the alkali salt formed during step (a) with an equimolar amount of l-N-benzyl-2-amino-butanol to the amount of the l-trans isomer present in the isomeric mixture to form the l-trans-2,2-dimethyl-3-(2,2-vinyl)-cyclopropane carboxylic acid-l-benzyl-2-amino-butanol as a crystalline salt;

(c) filtering the crystalline salt from the solution containing the optically active antipode;

(d) applying a mineral acid to decompose the crystalline salt; and (e) recovering the l-trans-2,2-dimethyl-3-(2,2-vinyl)-cyclopropane carboxylic acid.

9. The process defined in claim 5 wherein the optically active antipode in the filtrate formed in step (c) is recovered.

10. The process defined in claim 6 wherein the optically active antipode in the filtrate formed in step (c) is recovered.

11. The process defined in claim 7 wherein the optically active antipode in the filtrate formed in step (c) is recovered.

12. The process defined in claim 8 wherein the optically active antipode in the filtrate formed in step (c) is recovered.

13. A process for separating the optically active cis-trans isomers of a 2,2-dimethyl-3-(2,2-vinyl)-cyclopropane carboxylic acid of the formula (I)

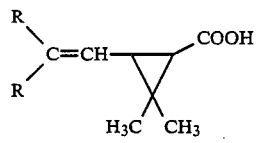

wherein R is halogen or methyl; which comprises the steps of:

(a) reacting an aqueous solution of a salt of the formula (I) racemate, containing the cis-trans isomers in any ratio formed with 1.2 to 1.3 equivalents of an alkali hydroxide with d-N-benzyl-2-amino-butanol taken in an amount equivalent to the d-trans content of said racemate and dissolved in an aliphatic ketone at a temperature of 40° to 60° C.;

(b) obtaining the crystalline d-trans isomer of the formula (I) in the form of its d-N-benzyl-2-amino butanol salt after cooling by filtration;

(c) decomposing said salt of the d-trans isomer of the formula (I) by using a mineral acid, then separating out the d-trans isomer of the compound of the formula (I);

(d) adding to the filtrate formed in step (b) l-N-benzyl-2-amino-butanol in an amount equivalent to the l-trans isomer content of the compound of the formula (I) present in the filtrate;

(e) obtaining the crystalline l-trans isomer of the formula (I) in the form of its l-N-benzyl-2-amino-butanol salt after cooling by filtration;

(f) decomposing said salt of the l-trans isomer of the formula (I) by acidifying the aqueous suspension thereof, then separating out the l-trans isomer of the compound of the formula (I);

(g) resolving the dl-cis racemate of the compound of the formula (I) remaining in the filtrate formed in step (e) by adding an aqueous solution of 0.4 to 0.6 equivalents of d-N-benzyl-2-amino butanol at a temperature of 40° to 90° C. along with 1.2 to 1.3 equivalents of an alkali hydroxide or alkali carbonate;

(h) obtaining the crystalline l-cis-isomer of the compound of the formula (I) in the form of its d-N-benzyl-2-amino butanol salt after cooling by filtration;

(i) decomposing the salt of the l-cis isomer of the formula (I) formed in step (h) by acidifying the aqueous suspension thereof, then separating out the l-cis isomer of the formula (I); and (j) evaporating the filtrate formed in step (h) to recover the d-cis isomer of the formula (I).

14. The process defined in claim 13 wherein the d-N-benzyl-2-amino butanol or the 1-N-benzyl-2-amino butanol are recovered in high purity removing any organic solvents by boiling and clarifying the acidic aqueous solutions remaining after separation of the optically active isomers of the of the formula (I) in the resolving process, by adding alkali to increase the pH to 10.

15. The process defined in claim 13 wherein it is desired to obtain an optically active cis or trans isomer of the formula (I) in high purity, which further comprises the following steps:

(a) selectively precipitating by adding at a temperature of 0° to 10° C. an amount less than equivalent of a mineral acid, as calculated from the optical purity of the optically active cis or trans isomer, to an aqueous solution of an alkali salt of the isomer;

(b) separating the precipitated optically active cis or trans isomer to obtain two fractions, a first fraction containing a filtrate and a second fraction containing a precipitate, wherein in the case of a cis isomer the first fraction contains a racemate whereas in the case of a trans isomer the first fraction contains optically pure isomer.

16. A process for obtaining a compound of the formula (I) in high concentration of its cis isomer

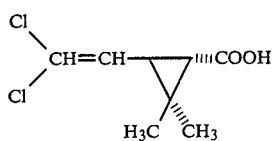

from a racemic cis-trans mixture thereof, which comprises the following steps:
(a) stirring the racemic cis-trans mixture of the compound of the formula (I) in benzene at 20° to 30° C. to form a suspension; and
(b) filtering the suspension to yield a solid product containing the compound of the formula (I) in high concentration of its cis isomer.

17. A process for obtaining a compound of the formula (I) in high concentration of its trans isomer

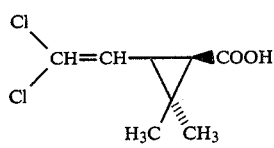

from a racemic cis-trans mixture thereof, which comprises the following steps:
(a) stirring the racemic cis-trans mixture of the compound of the formula (I) in benzene at 20° to 30° C. to form a suspension;
(b) filtering the suspension to obtain a filtrate richer in the racemic trans isomer of the formula (I), than the starting material;
(c) evaporating the benzene from the filtrate to recover the compound of the formula (I) richer in the racemic trans isomer;
(d) stirring the compound of the formula (I) richer in the racemic trans isomer with n-hexane to form a suspension; and
(e) filtering the suspension to obtain the compound of the formula (I) in solid form in high concentration of the trans isomer.

18. A process for the preparation of a compound of the formula (I) in high concentration of its cis isomer

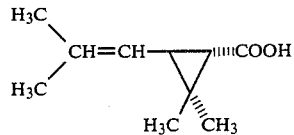

from a racemic cis-trans mixture thereof, which comprises the following steps:
(a) stirring the racemic cis-trans mixture of the compound of the formula (I) in n-hexane to form a suspension; and
(b) filtering the suspension to yield a solid product containing the compound of the formula (I) in high concentration of its cis isomer.

19. A process for the preparation of a compound of the formula (I) in high concentration of its trans isomer

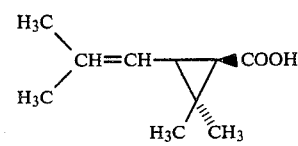

from a racemic cis-trans mixture thereof, which comprises the following steps:
(a) stirring the racemic cis-trans mixture of the compound of the formula (I) in n-hexane to form a suspension;
(b) filtering the suspension to yield a filtrate high in the racemic trans isomer; and
(c) evaporating the n-hexane from the filtrate to recover the compound of the formula (I) high in the racemic trans isomer.

* * * * *